(12) United States Patent
Plotkin et al.

(10) Patent No.: US 6,497,841 B1
(45) Date of Patent: Dec. 24, 2002

(54) PREVENTION OF ELECTRICAL DISCHARGES IN POLYMERIC HEAT EXCHANGERS

(75) Inventors: Neil D. Plotkin, Pasadena, CA (US); Roger J. Elgas, Anaheim, CA (US); Robert F. Gremel, Huntington Beach, CA (US); Robert V. Worrell, Lake Forest, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 08/898,559

(22) Filed: Jul. 22, 1997

(51) Int. Cl.[7] .................................................. A61M 1/14
(52) U.S. Cl. ........................... 422/46; 422/44; 422/45; 604/6.13
(58) Field of Search ........................ 422/44–48; 165/46, 165/11.1, 164, 148; 604/4.01, 6.13

(56) References Cited

U.S. PATENT DOCUMENTS 4,814,702 A * 3/1989 Driggers et al. ....... 324/207.16
5,127,907 A * 7/1992 Coutre et al. ................ 361/212
5,270,004 A * 12/1993 Cosentino et al. ..... 128/DIG. 3

FOREIGN PATENT DOCUMENTS

WO     Wo 97/25080     7/1997   ........... A61M/1/16

* cited by examiner

Primary Examiner—Angela D. Sykes
Assistant Examiner—Leslie Deak
(74) Attorney, Agent, or Firm—Thomas G. Berry; Daniel W. Latham (57) ABSTRACT

A heat exchanger, or the heat exchanger component of a multi-function device, comprising a polymeric heat transfer material. The heat exchanger exhibits reduced voltage-induced breakdown of the polymeric material, which can lead to cross-contamination of the two fluids. Either or both of two approaches may be employed. The first approach modifies the polymeric material to increase its resistance to breakdown. The second approach employs at least one electrical bridge between the fluids in the two sides of the heat exchanger, thus placing the two fluids into electrical equilibrium.

88 Claims, 10 Drawing Sheets

PREVENTION OF ELECTRICAL DISCHARGES IN POLYMERIC HEAT EXCHANGERS

TECHNICAL FIELD

This invention relates to heat exchangers for physiologic fluids such as blood and blood-related fluids. Examples include stand alone heat exchangers used to maintain a patient's blood at a predetermined temperature; the heat exchanger components of other devices, such as oxygenators used to maintain a patient's blood at a predetermined temperature while replacing carbon dioxide in the blood with oxygen; heat exchangers used to cool cardioplegia solutions; and the like.

BACKGROUND

Heat exchangers of the well-known "shell and tube" type are widely used in the medical field for physiologic fluids, such as blood, blood-related fluids, blood-based and non-blood based cardioplegia solutions (including crystalloid solutions), cell culture media, cell suspensions, proteins, and microcapsule suspensions. (For convenience, the term "blood" should be understood to include all such types of fluids unless specifically indicated otherwise.) Typically, the physiologic fluid is continuously or intermittently pumped through the heat exchanger and a suitable heat transfer fluid such as water is also pumped through the heat exchanger, physically separated from the physiologic fluid but capable of releasing or absorbing energy to or from the physiologic fluid. The water is either heated or cooled externally of the heat exchanger to maintain the physiologic fluid at a predetermined desired temperature.

One type of heat exchanger comprises tiny hollow fibers made of a polymeric material. Water entering the heat exchanger may flow around the outside surfaces of these fibers, while the physiologic fluid flows inside the fibers, or vice versa. The portion of the heat exchanger containing fluid which flows inside the fibers is known as the "tube" side, and the portion of the heat exchanger containing fluid which surrounds the fibers is known as the "shell" side.

SUMMARY OF THE INVENTION

The first general embodiment of the invention is a polymeric heat exchange material which has higher resistance to elecrical discharge through the material. The second general embodiment of the invention is a method and apparatus for maintaining electrical charge equilibrium between the "tube" side and the "shell" side of a polymeric heat exchanger, but the invention is not limited to only the tube-and-shell type of heat exchangers. The method comprises any technique for creating at least one electrical bridge between the tube side and the shell side. The apparatus comprises at least one electrical bridge between the tube side and the shell side. The only substantive requirement for the electrical bridge is that it permits sufficient current density to reduce the charge differential (or voltage potential) between the tube side and the shell side to a level below that at which electrical charge-induced breakdown of the polymeric material occurs. Since it is only necessary to equalize the charge between the tube and shell sides of the heat exchanger, an earth ground is not required. The two general embodiments may be employed separately or in combination.

DETAILED DESCRIPTION

The principles of the invention can be applied to various designs of heat exchangers. As a matter of convenience, the following description often refers to the two sides of a heat exchanger as the "tube" side and the "shell" side, but the invention is not limited to the specific "shell and tube" type. The invention is broadly applicable to any type of heat exchanger in which a polymeric material separates a "subject" physiologic fluid (ie., a physiologic fluid heated or cooled by thermal energy transfer across the polymeric material) from a heat exchange fluid. Examples include, but are not limited to, pleated (or "Z-folded") film heat exchangers, flat plate heat exchangers, corrugated heat exchangers, and multilayer polymeric film heat exchangers (such as that disclosed in International Application No. PCT/GB96/02189, the entirety of which is incorporated by reference). The exact chemistry of the polymeric material is also determined by conventional principles, polycarbonates, polypropylenes, polyurethanes, and polyethylenes being commonly used (but non-limiting) examples.

Some medical devices use non-porous polymeric tubing (sometimes called "microtubing"), also known as hollow fibers, as heat exchanger elements in "shell and tube" and other configurations. Such polymeric tubular heat exchangers have advantages over finned, convoluted, tubular, or other metal (typically stainless steel or aluminum) heat exchangers, primarily increased surface area for heat transfer and lower priming volume per unit volume of the device; improved biocompatibility; and lower manufacturing cost.

Such heat exchangers can be stand alone heat exchangers used to maintain a physiologic fluid (such as a patient's blood) at a predetermined temperature, or the heat exchanger components of oxygenators used to maintain a patient's blood at a predetermined temperature while replacing carbon dioxide in the blood with oxygen; or heat exchangers used to cool physiologic fluids such as cardioplegia solutions; and the like. Unless noted specifically to the contrary, the term "heat exchanger" includes all such devices whether standing alone or forming components of more complex systems.

Commercially available examples of such complex systems include the MAXIMA FORTÉ oxygenator available from Medtronic, Inc. of Minneapolis, Minn., USA, in which the blood flows inside polymeric microtubing surrounded by water; and the WILLIAM HARVEY model HF-5700 blood oxygenator available from C. R. Bard, Inc. of Murray Hill, N.J., USA, in which the blood flows outside polymeric tubes that contain a flow of temperature-regulated water. Other examples are the QUADROX fiber oxygenator and the integral or stand alone heat exchangers (employing star-shaped polyethylene capillaries) forming part of the "M-series" (M2, M5, M8, M16, and M30) membrane oxygenators, all manufactured by Jostra Medizintechnik AG of Hirrlingen, Germany; the HPO-25H oxygenator manufactured by Mera of Japan; and the BIOCOR 200 oxygenator manufactured by Minntech Corporation of Minneapolis, Minn., USA.

Other examples of oxygenator designs in which a heat exchanger incorporating the principles of the invention may be advantageouare disclosed in U.S. Pat. No. 5,429,184 (Bach et al.), U.S. Pat. No. 5,429,802 (Hagiwara et al.), U.S. Pat. No. 5,468,449 (Sjogren et al.), U.S. Pat. No. 5,470,531 (Sjogren et al.), U.S. Pat. No. 5,162,101 (Cosentino et al.), U.S. Pat. No. 5,137,531 (Lee et al.), U.S. Pat. No. 5,240,677 (Jones et al.), U.S. Pat. No. 5,578,267 (Cosentino et al.), and U.S. Pat. No. 5,270,004 (Cosentino et al.), all of which are entirely incorporated by reference.

Examples of cardioplegia heat exchangers include the CARDIOTHERM cardioplegia heat exchanger available from Medtronic, Inc. of Minneapolis, Minn., USA. Other cardioplegia delivery systems are disclosed in U.S. Pat. No. 5,403,281 (O'Neill et al.), U.S. Pat. No. 5,540,841 (Gsell et al.), U.S. Pat. No. 5,609,571 (Buckberg et al.), and U.S. Pat. No. 5,643,191 (Buckberg et al.), all of which are entirely incorporated by reference.

A non-limiting example of a system for processing other types of physiologic fluids is that disclosed in U.S. Pat. No. 5,630,946 (Hart et al.), which is entirely incorporated by reference.

It should be noted that many existing device designs (including but not limited to the devices described in this application) may not incorporate a polymeric heat exchanger. Modified versions of such devices that incorporate a polymeric heat exchanger having the improvements described below are within the scope of the invention. Similarly, the device designs described in this application comprise design elements and features which may be combined into new devices incorporating practice of this invention.

By coincidence, the polymeric materials used in the heat exchangers are electrical insulators. Thus, any electrical voltage or potential generated for any reason may be maintained on the microtubing during set up and use of the device. Several mechanisms may be involved in the creation of such a potential, including failure of any insulation present on the polymeric microtubing; failure of any ground circuit provided; or charge generation due to passage of liquids through an electrically isolated fluid path; or piezoelectric effects on polymer crystals in pumps. Regardless of the mechanism by which they are created, these voltages can exceed the breakdown voltage of the plastic heat exchanger material. This causes an electrical discharge through the microtubing wall, thus creating a hole in the plastic material. If such a hole lies between the shell side and the tube side of the heat exchanger, cross-contamination of the fluids on the respective sides of the heat exchanger can occur, possibly leading to an adverse impact on the operation of the device and perhaps even on the health of the patient.

Therefore, one may implement the invention by reducing, preferably eliminating, the voltage potential between the tube side and the shell side to prevent failure of the polymeric tubing. There are two general embodiments of the invention, which may be practiced separately or together.

The first general embodiment of the invention is a polymeric heat exchange material which has higher resistance to elecrical discharge through the material. This can be accomplished by using a thicker material, provided that other factors (notably heat exchange performance) are not too greatly affected. It is also possible to treat the polymeric material to increase its resistance to failure. Coating the material with a suitable material is one example, as is "doping" or otherwise introducing into the composition of the material suitable additives to increase its resistance to failure.

The other general embodiment of the invention is an electrical bridge between the shell side and the tube side that at least reduces the voltage potential between them to less than the level that may cause failure of the polymeric tubing material. In the preferred embodiment, the electrical bridge keeps the tube side and the shell side at a common electrical potential. Any type of electrical bridge is within the scope of the invention. Any method of reducing the voltage potential between the tube side and the shell side is within the scope of the invention. Any apparatus that reduces the voltage potential between the tube side and the shell side is within the scope of the invention. Any method of eliminating the voltage potential between the tube side and the shell side is within the scope of the invention. Any apparatus that eliminates the voltage potential between the tube side and the shell side is within the scope of the invention.

Figure 1:
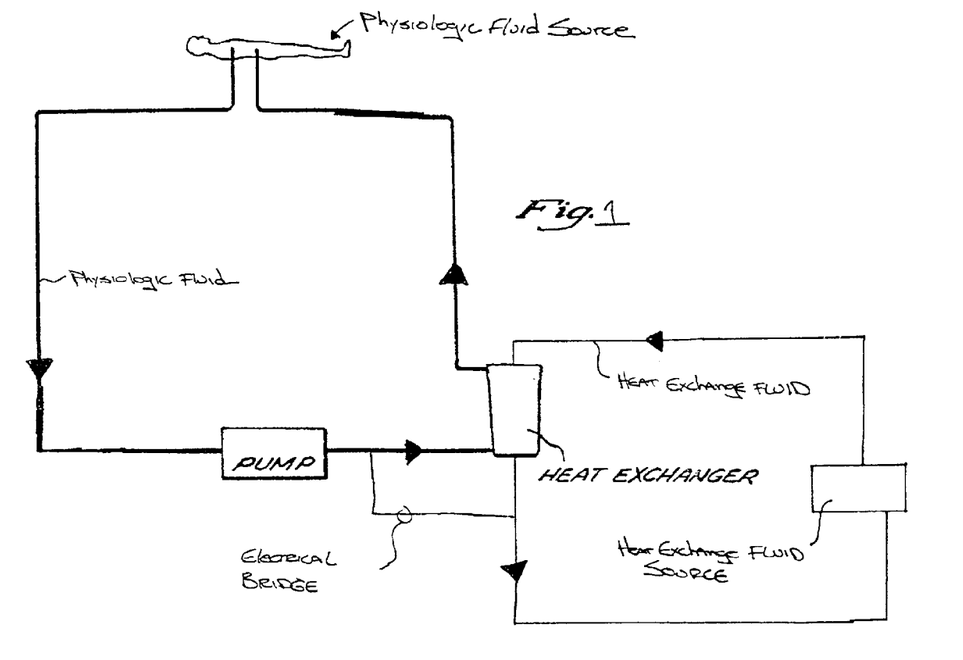
FIG. 1 is a schematic representation of the invention.

FIG. 1 is a schematic illustration of the invention. (Of course, a more complex blood handling circuit would be employed in cardiac bypass surgery, such as the arrangement shown in FIG. 5 of U.S. Pat. No. 5,084,244 (Muramoto), which patent is incorporated in its entirety by reference.)

Physiologic fluid from a source schematically indicated as a patient is pumped to a heat exchanger and back to the source. In principle, the pump can be any of the conventional types of physiologic fluid pumps, such as centrifugal pumps, roller pumps, etc., although for reasons not fully understood at this time, practice of the invention appears to be unnecessary unless a roller pump is used. Similarly, for reasons not fully understood at this time, practice of the invention may require the polymeric tubing used to convey the physiologic fluid through the roller pump to be a material based on polyvinylchloride (PVC) or silicon. The voltage potentials in devices attached to PVC tubing has been measured at up to 1700 volts; and up to 40 volts in similar tests using silicon tubing. Also, the conductivity of the heat exchange fluid does not appear to be relevant to practice of the invention, as there has been no significant difference observed between deionized water and ordinary tap water as heat exchange fluids.

A heat exchange fluid from an appropriate source also passes though the heat exchanger as indicated by the arrows. The relative directions of the physiologic fluid and the heat exchange fluid as each passes into and out of the heat exchanger are arbitrary, as are the choice of whether the physiologic fluid enters the top or bottom of the heat exchanger, and whether the heat exchange fluid enters the top or the bottom of the heat exchanger. Also, one of the fluids will be in the shell side of the heat exchanger and the other fluid will be in the tube side of the heat exchanger, but the choice of which fluid is in which side is arbitrary as far as the invention is concerned. An electrical bridge between the heat exchange fluid path and the physiologic fluid path eliminates the problem of the two paths having a voltage potential between them.

Specific embodiments of the invention include, but are not limited to, single point grounding; multipoint grounding; fusible linkages; modification of the grounding to improve bonding; biocompatibility, or to set a threshold voltage for discharge. Preferably, the common potential is significantly less than the breakdown voltage of the polymeric material, and sufficiently low to avoid creating electrical interference in nearby medical instruments or adverse electrical hazards to the patient.

The most preferred embodiment uses a floating ground instead of earth ground (zero potential) as the common potential level. This is consistent with the philosophy that the patient should not be attached to earth ground during a surgical procedure, lest a short circuit in any electrical device reach the patient though the earth ground. However, in retrofit situations, there may be an existing earth grounded connection which is conveniently used to implement the invention. In such situations, the preference for a floating ground may defer to the preference for as little modification as possible to implement the invention, especially if other protection for the patient can be provided.

Thus, several broadly defined embodiments are possible. In the first, most preferred embodiment, an electrical bridge connects only the tube side to the shell side, which places them at the same non-ground potential. In the second, less preferred embodiment, an electrical bridge between the tube side and earth ground is added to the first embodiment. In the third, also less preferred, an electrical bridge between the shell side and earth ground is added to the first embodiment. In the fourth, again less preferred, electrical bridges between both the tube side and the shell side and earth ground are added to the first embodiment.

The following specific types of electrical bridges are possible for any or all of the electrical bridges described in the broad embodiments described immediately above. First, a simple conductor (such as a common wire) is added to the appropriate locations on the external surfaces of the medical device, using fittings as appropriate to the circumstances. This is a simple way to implement the invention in the field to existing medical devices previously manufactured without integrating the invention into the design and manufacture of the device. Second, any form of electrical bridge can be incorporated into the interior of the device. For example, a conductive wire, ribbon, or film could be used. Since the conductor will be subjected to stresses present in the device itself, it is preferred that the electrical bridge be formed into a suitable configuration to provide adequate strain relief against thermal expansion and contraction, or improved mechanical retention. Acceptable configurations include, but are not limited to, a straight wire; at least one coil; sinusoidal patterns; at least one Z-shaped fold, swagged shapes, and the like. It is possible for the electrical bridge to be located at the upper end of the device, the lower end of the device, or at both ends of the device.

The electrical bridge may be attached to, or molded into the plastic casing or housing of the device such that only the ends of the conductor are exposed for connection to the tube side and the shell side, respectively. Such attachment or molding may be accomplished in any manner, including but not limited to any mechanical fixing technique, friction coupling, ultrasonic attachment or welding, insert molding, use of adhesives, etc. The electrical bridge can be an exposed portion of interfaces between a housing and a shell side or tube side when all such parts are manufactured from electrically conductive materials. The electrical bridge can be conductive material such as ink or paint applied to the device. The electrical bridge can be a metallized fiber, screen, or other complex and/or multilayer construction.

The electrical bridge can be a conductive material such as a conductive plastic or polymer, either an inherently conductive material, or one which comprises electrically conductive filler materials of any otherwise suitable type. The electrical bridge can be an electrically or ionically permeable membrane between the shell and tube side.

The electrical bridge can be a metal conductor coated or otherwise imparted with a material having a lower dielectric constant than the polymeric fiber wall material, preferably providing improved bonding, or biocompatiblity, or both, while still protecting the fiber wall from damage due to electrical discharge. It is possible to tailor the material to provide a dielectric constant such that the electrical bridge will be made only above a minimum threshold value. Similarly, the electrical bridge can be a fusible material such that electrical current above a certain amount melts or otherwise interrupts the link, breaking the grounding circuit and thus protecting the patient.

In any embodiment, the electrical bridge may further comprise an indication that a voltage potential is present. Any and all of the conventional indicators can be used, such as an electromagnetic signal of any type, including but not limited to light or change of color. Similarly, the indicator can be an auditory indication, such as a sound. It is also possible for the indication to be an analog or digital signal transmitted to any suitable device to receive and indicate the signal.

In any embodiment, the electrical bridge can be made at one or more locations physically remote from, but electrically common to, the tube side, the shell side, or both. For example, a very preferred location for a connection to the tube side fluid is a metal probe, specifically the commonly used metal temperature sensor, located in the physiologic fluid downstream of the heat exchanger. Of course, the reverse is also possible, i.e., the electrical bridge to the tube side could be accomplished through any convenient technique, and the shell side fluid could be connected by the other end of the electrical bridge through an already present metal probe of any convenient type located at any convenient location.

The electrical bridge may be a conductive stainless steel or carbon thread located inside the heat exchanger. Examples of suitable locations include placement next to the polymeric heat exchanger fibers prior to addition of a potting material; or even more preferably, placement within the mat of polymeric fibers itself prior to assembly of the heat exchanger bundle.

The electrical bridge may comprise a conductive potting material serving the dual roles of a conventional potting material (sealing, etc.) and an electrical bridge. Thus, otherwise conventional potting materials may be made conductive by any convenient technique, including (without limitation) addition of electrical particles, shavings, and the like.

OXYGENATOR EXAMPLE

A preferred embodiment of the invention may be illustrated by considering the design of the MAXIMA FORTÉ oxygenator available from Medtronic, Inc. of Minneapolis, Minn., USA. Of course, details described below that are specific to this device, but not necessary to practice of the invention, may be different in other embodiments of the invention. In particular, it is possible to construct a stand alone heat exchanger, in accordance with the invention, that is adapted to be used with a stand alone oxygenator not having a built in heat exchanger, but otherwise in general accordance with the embodiment illustrated below.

Figure 2:
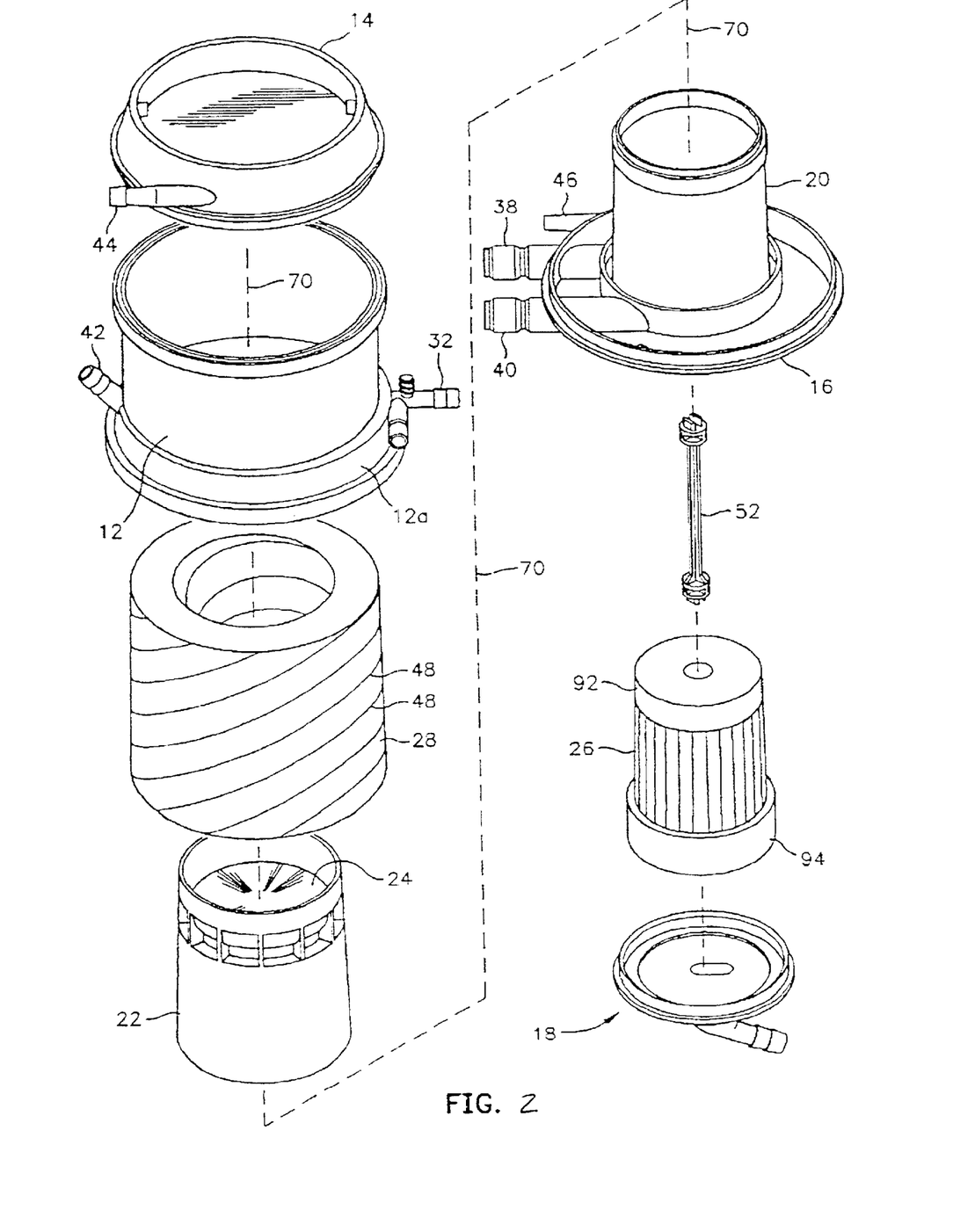
FIG. 2 is an exploded isometric view of a blood oxygenator constructed in accordance with this invention.
Figure 3:
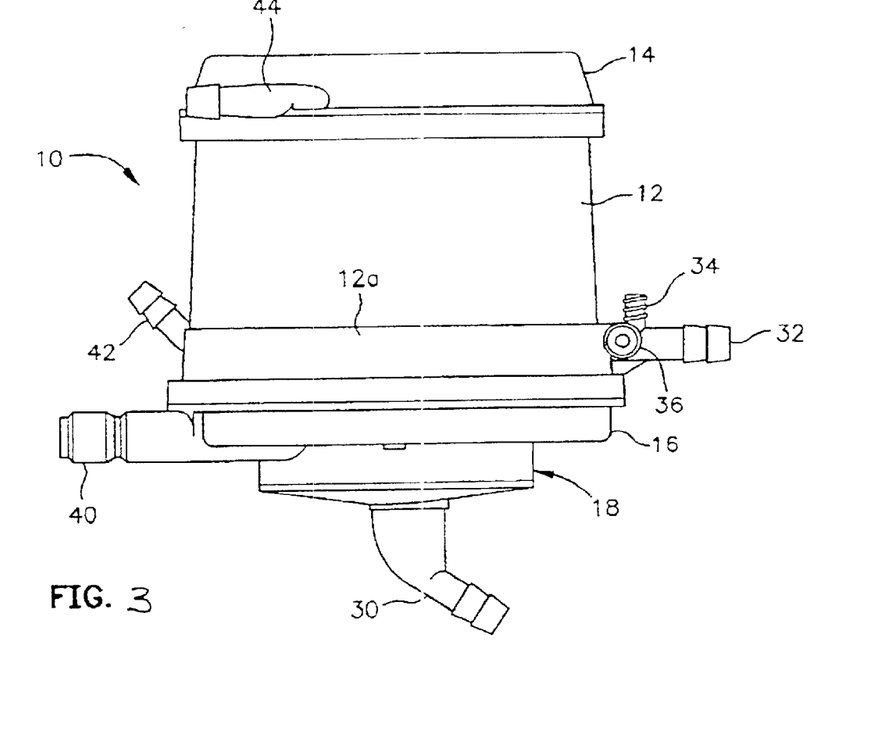
FIG. 3 is a side elevation view of the assembled blood oxygenator of FIG. 2.
Figure 4:
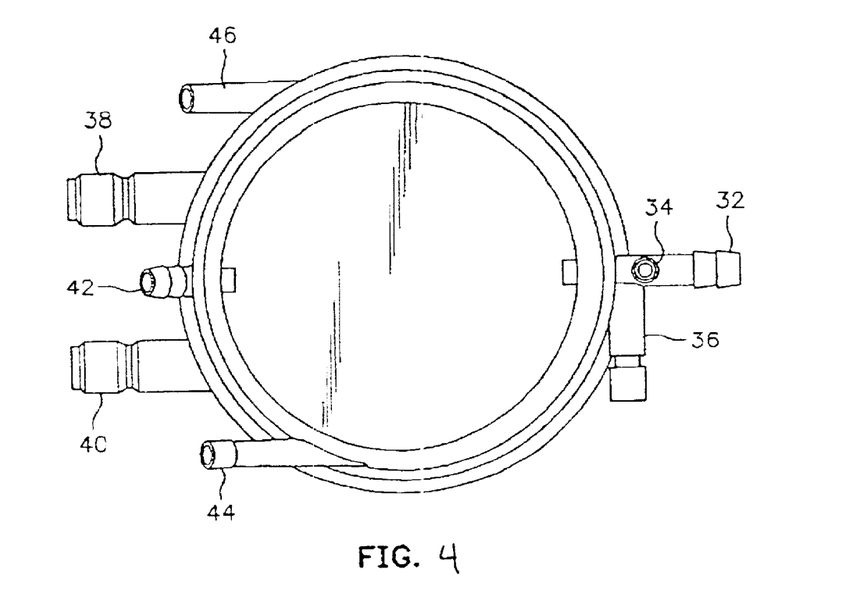
FIG. 4 is a top plan view of the blood oxygenator of FIG. 3.

Referring to FIGS. 2–4, a blood oxygenator 10 comprises an outer generally cylindrical vessel 12 which is sealed at its upper end by a generally saucer-shaped upper hollow venous gas header 14. A generally saucer-shaped lower hollow venous gas header 16 seals the lower end of the vessel 12. A blood inlet manifold 18 is connected to the center of the underside of the lower venous gas header 16. Concentric, generally cylindrical inner and outer heat exchanger housings 20 and 22 are connected at their lower ends to the center of the lower venous header 16. The upper end of the outer heat exchanger housing 22 includes a transition manifold 24. The interior of the inner heat exchanger housing 20 surrounds and encloses a generally cylindrical first fiber bundle 26 made up of a plurality of vertically oriented hollow micro-conduits. These micro-conduits convey blood vertically upward. A second generally cylindrical fiber bundle 28 concentrically surrounds the outer heat exchanger housing 22 and is positioned inside the inner wall of the cylindrical vessel 12. The upper and lower ends of the generally ring-shaped second fiber bundle 28 interact with the upper and lower venous gas headers 14 and 16, respectively.

The blood inlet manifold 18 (FIG. 3) includes a barbed blood inlet nozzle 30 which bends downwardly at an angle relative to the central vertical axis of the vessel 12. A barbed blood outlet nozzle 32 (FIGS. 3 and 4) extends horizontally from the exterior of an enlarged or flared portion 12a of the vessel 12. A standard leur fitting 34 (FIG. 3) extends vertically from the base of the blood outlet nozzle 32. A thermometer probe fitting 36 (FIG. 4) extends horizontally from the base of the blood outlet nozzle 32.

Inlet and outlet nozzles 38 and 40 (FIGS. 2 and 4) for a heat transfer fluid such as water extend horizontally from one side of the low venous gas header 16 and communicate with water flow passages inside the inner heat exchanger housing 20. A barbed de-bubbler nozzle 42 (FIG. 3) extends upwardly at an angle from the flared portion 12a of the vessel 12. A gas mixture inlet nozzle 44 (FIGS. 2, 3 and 4) extends horizontally from the periphery of the upper venous gas header 14. A gas mixture outlet nozzle 46 (FIGS. 2 and 4) extends from the periphery of the lower venous gas header 16 parallel to the water inlet and outlet nozzles 38 and 40.

Figure 5:
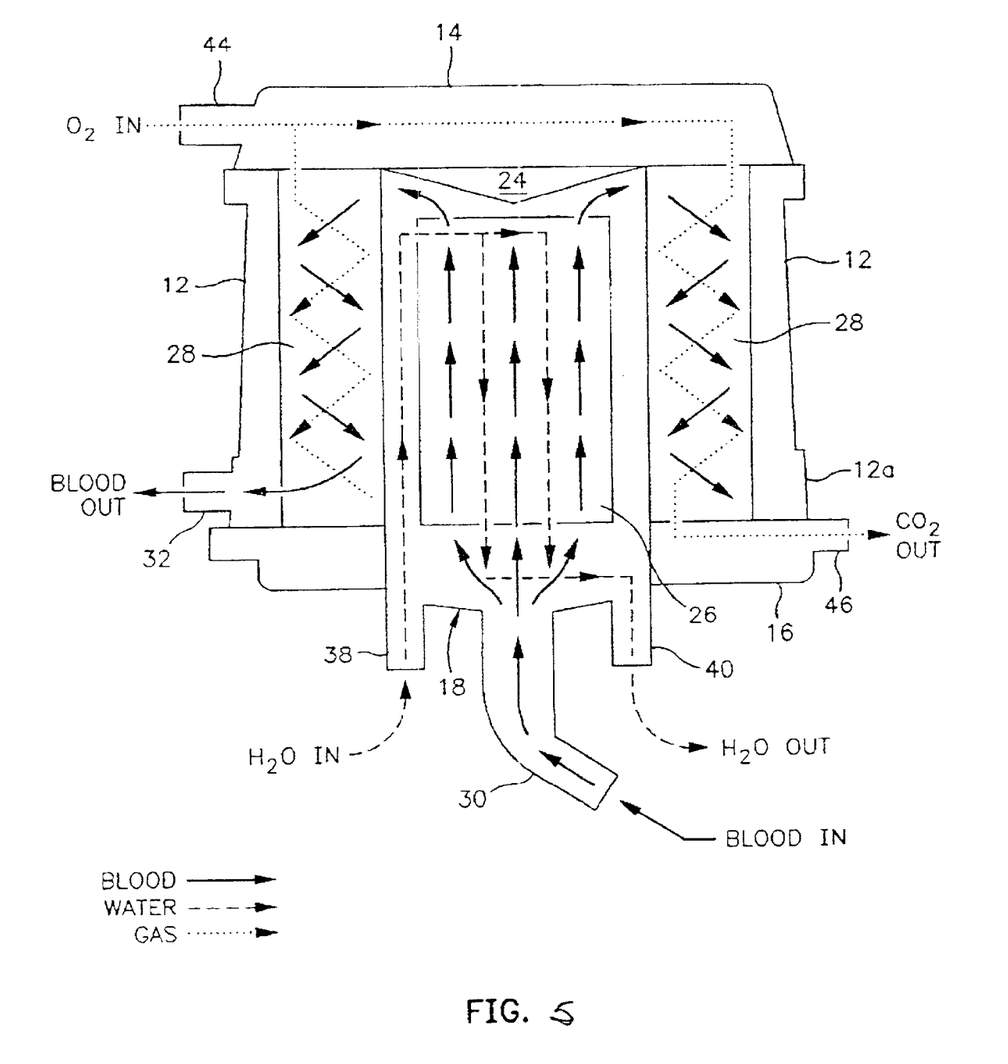
FIG. 5 is a diagrammatic view illustrating the blood, heat transfer fluid and gas mixture flow paths of the blood oxygenator of FIGS. 2–4.
Figure 6:
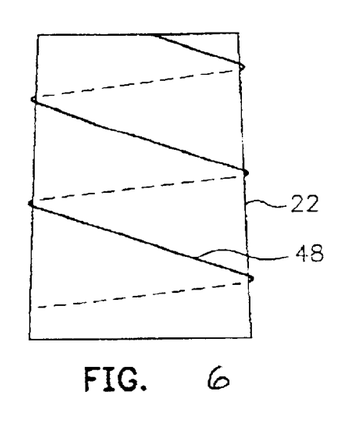
FIG. 6 is a diagrammatic view illustrating the fabrication of the oxygenator fiber bundle of the blood oxygenator of FIGS. 2–5.

The blood, heat transfer fluid and gas mixture flow paths of the blood oxygenator 10 can best be understood by way of reference to the diagrammatic vertical sectional view of FIG. 5. In that figure, the flow of blood is illustrated diagrammatically by the bold solid arrows. The dashed lines illustrate the flow of heat transfer fluid (water). The flow of gas mixture is illustrated by the sequence of dots. Blood from the patient flows through tubing (not illustrated) connected to the blood inlet nozzle 30. This incoming blood spreads out through the blood inlet manifold 18 and travels vertically through the micro-conduits of the first fiber bundle 26 of the central heat exchanger that forms the core of the blood oxygenator 10. Water flows in through the inlet nozzle 38 vertically to the top of the heat exchanger fiber bundle 26 through a separate channel isolated from the fiber bundle 26. The water is then directed down and across the outside of the micro-conduits of the fiber bundle 26. The water flows around the outside of the micro-conduits opposite the flow of the blood within the micro-conduits. The water exiting from the lower end of the first fiber bundle 26 exits through the outlet nozzle 40.

The water is heated or cooled outside the blood oxygenator, as necessary to regulate the temperature of the blood flowing through the micro-conduits of the heat exchanger. The use of a counter-flow heat exchanger provides optimum heat exchange efficiency. However, as noted above, the counter-flow design is not essential to the invention.

The temperature of the blood can be monitored by a circuit (not illustrated) that includes a thermistor or other temperature sensing device (not illustrated) mounted inside the thermometer probe fitting 36 (FIGS. 3 and 4). The thermometer probe fitting 36 is a preferred location for connection of an electrical bridge to the blood side of the heat exchanger, since the temperature sensing device is likely to be coincidentally an electrically conductive material (typically metal) already in physical contact with the blood. Thus, the invention may be implemented by connecting a conductive bridge between the temperature sensing device and any convenient location on the other side of the heat exchanger.

Blood exiting from the upper end of the first fiber bundle 26 (FIG. 5) of the heat exchanger is directed radially outwardly by the transition manifold 24. This blood then travels around the outside of the fibers of the second fiber bundle 28 that forms the oxygenator. The blood travels downwardly past the outside surfaces of the fibers of the second fiber bundle 28. When the blood reaches the lower portion of the second fiber bundle 28, it is collected in an outlet manifold defined by the flared portion 12a of the vessel and exits through the blood outlet nozzle 32. The blood outlet nozzle 32 is connected to tubing (not illustrated) for returning the blood to the patient.

A gas mixture rich in oxygen from a pressurized source (not illustrated) is conveyed through a hose (not illustrated), through the gas mixture inlet nozzle 44, and into the upper venous gas header 14. The upper gas header 14 communicates with the upper ends of the fibers in the second fiber bundle 28 forming the membrane oxygenator. The oxygen-rich gas mixture travels down through the interior of the fibers in the fiber bundle 28. These fibers are micro-porous. Carbon dioxide from the blood surrounding the fibers in the bundle 28 diffuses through the walls of the fibers into the gas mixture. Similarly, oxygen from the gas mixture inside the fibers of the bundle 28 diffuses through the micro-pores into the blood. The gas mixture now having an elevated carbon dioxide content exits the lower ends of the fibers of the second fiber bundle 28 into the lower venous gas header 16 and then exits therefrom via the gas mixture outlet nozzle 46. This gas mixture now has a lower oxygen content. The nozzle 46 is connected to another gas hose (not illustrated).

Figure 7:
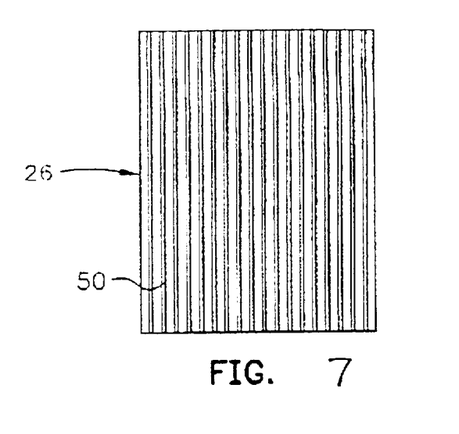
FIG. 7 is a diagrammatic view of the heat exchanger fiber bundle of the blood oxygenator of FIGS. 2–5.

FIG. 7 is a diagrammatic illustration of the first fiber bundle 26 which serves as the core of the heat exchanger portion of the blood oxygenator 10. The fiber bundle 26 has a generally cylindrical configuration and comprises approximately five thousand four hundred vertically (axially) extending hollow fibers 50. Preferably the fibers are provided as a continuous long web of microconduit wrapping material in which the fibers are held together by a thin, flexible, horizontally extending woven interconnect. Such wrapping material is commercially available from Mitsubishi Rayon, Co., Ltd. under the designation HFE430-1 Hollow Fiber. This material uses polyethylene fibers. Similar wrapping material is also commercially available from Hoechst Celanese Corporation under the designation Heat Exchanger Fiber Mat. This material uses polypropylene fibers.

The hollow fibers 50 (FIG. 7) of the heat exchanger fiber bundle 26 have an internal diameter which is so small, e.g., four hundred and twenty-eight microns, that the free flow of blood may be impaired due to the presence of trapped air bubbles. Accordingly, before using the heat exchanger, it is desirable to pass a wetting agent through the fibers 50. The wetting agent may comprise an ampiphilic molecule having one end, which is hydrophilic, and a second end, which is hydrophobic. An example of such a compound is hydrogenated phosphatidyl choline commercially available from Naderman Corporation under the trademark PHOSPOLIPON. This material has a USP grade and an FDA master file number, approving it for human intravenous use.

Figure 8:
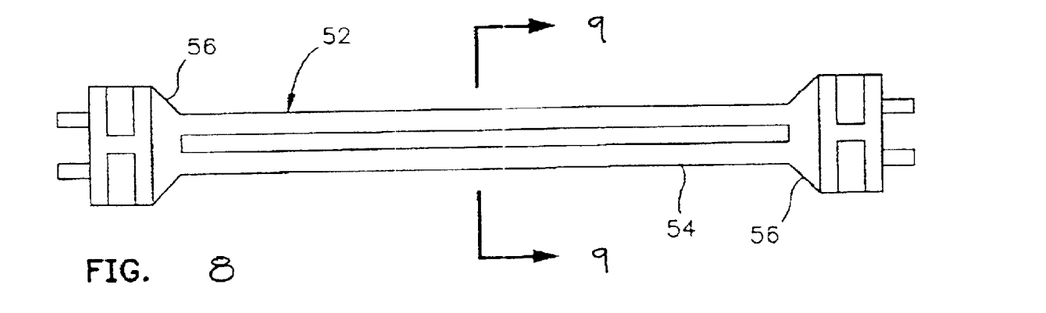
FIG. 8 is an enlarged side elevation view of the spindle of the heat exchanger of the blood oxygenator around which is wound the micro-conduit wrapping material.
Figure 9:
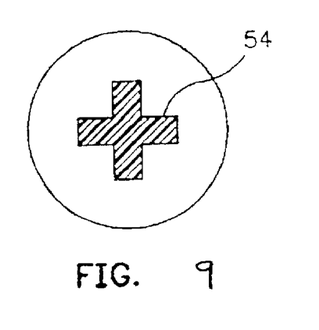
FIG. 9 is a cross-section view of the spindle of FIG. 8 taken along line 9—9 of FIG. 8.
Figure 10:
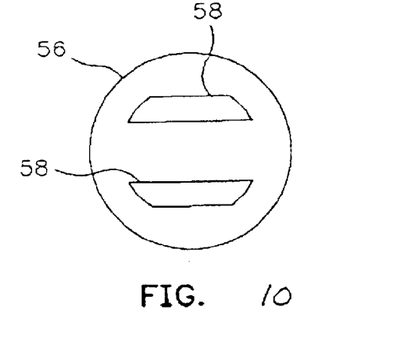
FIG. 10 is an end elevation view of the spindle of FIG. 8 taken from the right end of FIG. 8.

The micro-conduit wrapping material of the heat exchanger core is wound about a central, vertically orientated elongated spindle 52 (FIG. 8). The spindle 52 has an intermediate segment 54 having a cross-shaped cross-section, as best seen in FIG. 9. The spindle 52 has enlarged driving ends 56 connected to the opposite ends of the intermediate segment 54. Each of the driving ends 56 has a pair of parallel extending ribs 58 (FIG. 10) which are used to lock the spindle into a winding machine (not illustrated). This machine utilized to wind the micro-conduit wrapping material about the spindle 52. Preferably the micro-conduit wrapping material is compactly wound about the central spindle 52, but without any substantial tension on the web.

As mentioned above, the micro-conduit may be provided in a heat exchanger micro-conduit wrapping material. The wrapping material comprises micro-conduit fibers attached to a thin flexible interconnect, such as woven netting, to maintain the fibers at predetermined spacings in substantially parallel alignment with each other. The wrapping material is wrapped about an elongated spindle having first and second ends, such that the ends of each fiber reside proximate the spindle's first and second ends. After the ends of the fibers are trimmed as needed, a shell is placed around the wrapping material and spindle. Opposing first and second seals are created by applying potting compound between fibers proximate the spindle's first end and proximate the spindle's second end.

Figure 11:
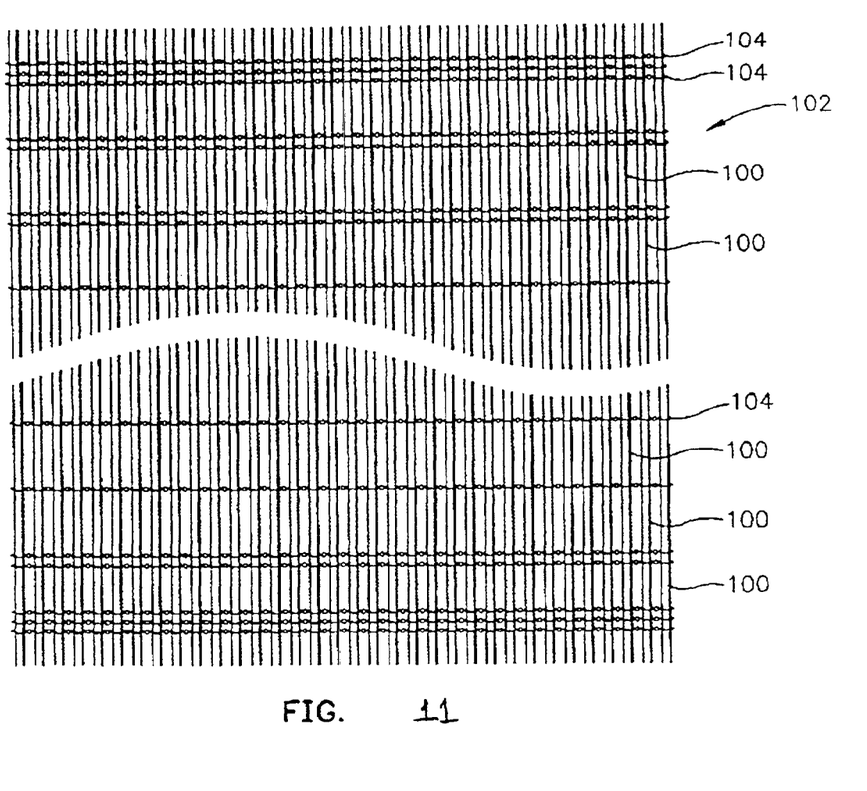
FIG. 11 is a side detail view of polymeric micro-conduit material suitable for construction of the bundle of FIG. 7.
Figure 12:
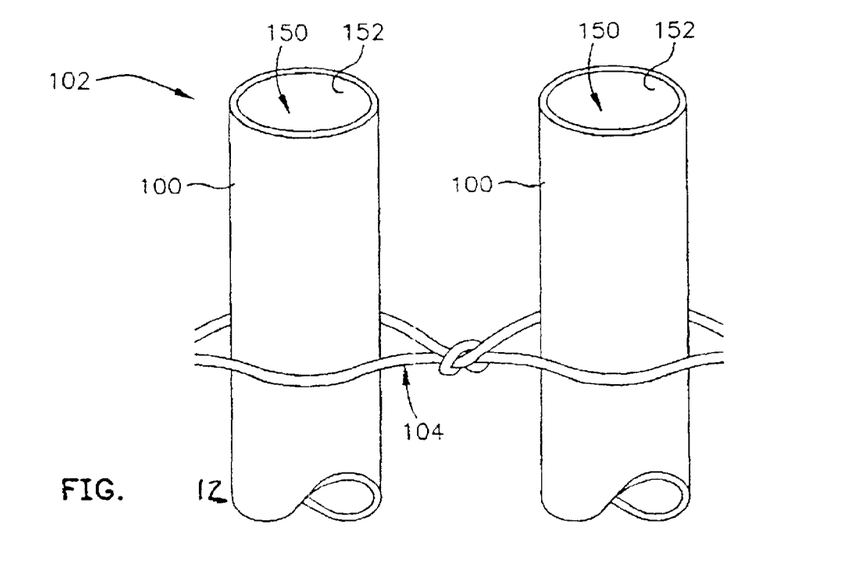
FIG. 12 is a magnified side detail view of a portion of the polymeric micro-conduit material of FIG. 11.
Figure 13:
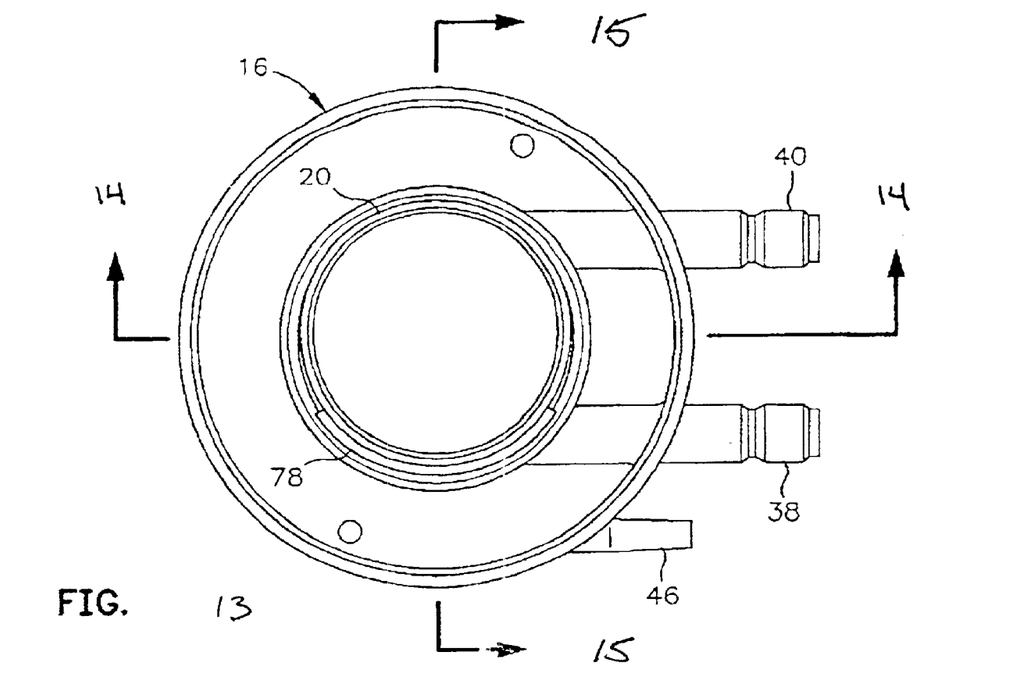
FIG. 13 is a top plan view of the lower venous gas header of the blood oxygenator. Also visible in this figure are the inner heat exchanger housing, the water inlet nozzle, the water outlet nozzle and the gas mixture outlet nozzle.
Figure 14:
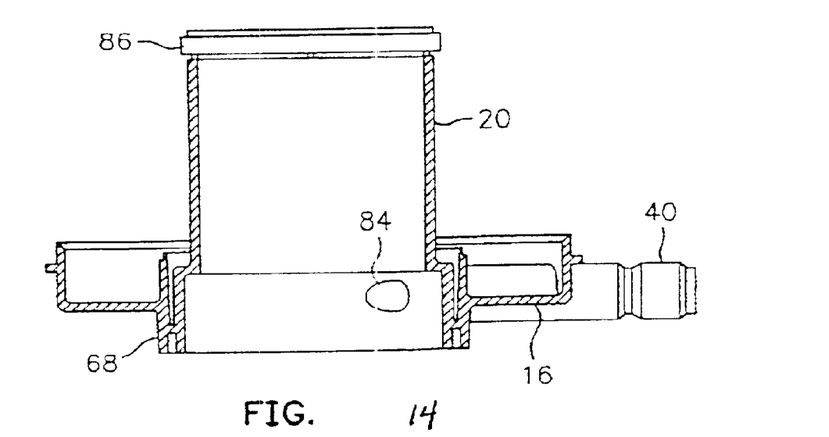
FIG. 14 is a sectional view of the lower venous gas header and inner heat exchanger housing taken along line 14—14 of FIG. 13.
Figure 15:
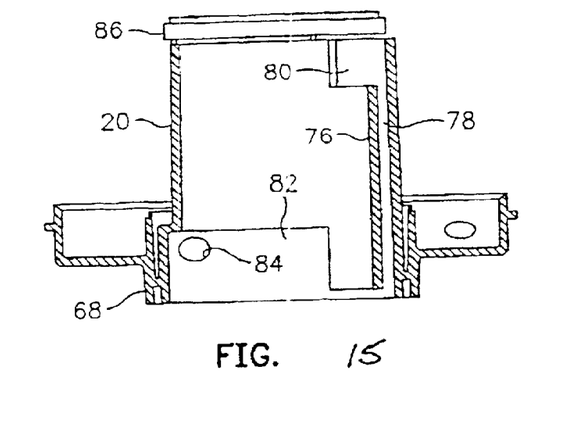
FIG. 15 is a sectional view of the lower venous gas header and inner heat exchanger housing taken along line 15—15 of FIG. 13.
Figure 16:
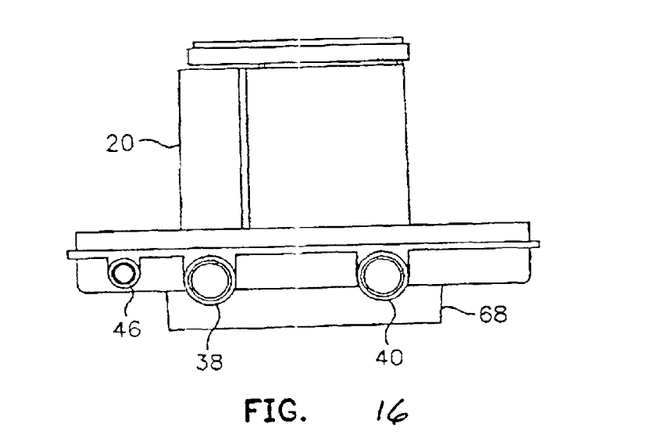
FIG. 16 is a front elevation view of the lower venous gas header and inner heat exchanger housing of the blood oxygenator.

A shown in detail in FIGS. 11 and 12, the heat exchanger micro-conduit, "micro-conduit" for short, preferably comprises a plurality of small fibers 100, as shown in FIG. 11. In FIG. 11, the fibers 100 are arranged in a "mat" of micro-conduit wrapping material 102, which is described in greater detail below. Each fiber 100 comprises an elongated two-ended fiber. Each fiber 100 is hollow, with a cross-sectional shape preferably being rounded, or alternatively triangular, rectangular, or another appropriate shape. Since the fibers 100 are hollow, each fiber 100 defines an inner channel 150 having an inner surface 152, as shown in FIG. 12. In the illustrated embodiment, the outer diameter of the fiber is about four hundred and seventy-five microns while the diameter of the inner channel 150 is about four hundred and twenty-eight microns. However, a wide variety of inner and outer diameters may be used, depending upon the requirements of the particular application. The difference between the inner and outer diameters is preferably small, to encourage heat exchange through the fibers' walls. The fibers 100 may be about ten centimeters long, for example. However, a wide range of fiber lengths may be used, depending upon the requirements of the particular application.

The fibers 100 may be made from a plastic material such as polypropylene, polyethylene, a different polymeric substance, or another material that is inexpensive, pharmacologically safe, lightweight, easily cut, and flexible. The material of the fibers 100 must also be easily formed into fibers with sufficiently small inner and outer dimensions. Preferably the fibers 100 would be made of a hydrophilic material, however, micro-conduit made of such material is not presently commercially available.

As mentioned above, FIG. 11 illustrates a section of micro-conduit wrapping material 102. The material 102 includes a thin flexible interconnect 104 that maintains the fibers 100 at predetermined spacings in substantially parallel alignment with each other. In the illustrated embodiment, the interconnect comprises substantially parallel lengths of flexible thread that are woven or knotted to hold the fibers about 0.5 mm apart, generally parallel to each other. The wrapping material 102 aids in positioning the fibers 100 during construction of a blood heat exchanger, as discussed below.

The mat or wrapping material 102 may be made of commercially available product from Mitsubishi Rayon Co., Ltd. sold under the designation HFE 430-1 Hollow Fiber, which uses polyethylene fibers. Similar wrapping material is also commercially available from Hoechst Celanese Corp. under the designation Heat Exchanger Fiber Mat, which uses polypropylene fibers.

To manufacture the blood heat exchanger, the micro-conduit wrapping material 102 is wrapped about the spindle, the fibers are installed into the shell, and the upper and lower seals are formed by injecting potting compound between the fibers 100 near the upper and lower surfaces of the core. Sufficient potting compound is applied to substantially seal the spaces between the fibers. Then, the fibers 100 are trimmed near each end of the spindle. Preferably, the trimmed fibers 100 form uniform flat upper and lower surfaces of the core. With the seals in place, liquids such as aqueous priming solution and blood may be directed into the fibers 100 through their ends, without leaking any liquid into the spaces between the fibers. Finally, the manifolds are attached to the shell. Also, hoses and other plumbing lines are attached to the heat exchanger 300 as needed, for transportation of heat exchange medium, blood, priming solution, oxygen, and other media as appropriate.

Generally, the heat exchanger regulates the temperature of a patient's blood during a medical procedure such as open heart surgery. Due to the large number of fibers 100 and the small size of the fibers, there is a substantial area of surface contact between the heat exchange medium and the contents of the fibers 100. The temperature of blood flowing through the core is efficiently regulated, due to the high degree of contact between the blood and the heat exchange medium.

The configuration of the lower venous gas header 16, the inner heat exchanger housing 20, the water inlet and outlet nozzles 38 and 40 and the gas mixture outlet nozzle 46, are illustrated in FIGS. 13–17. These parts, along with the raised annular wall member 68 that receives the blood inlet manifold 18, are all injection molded as a single unitary piece of plastic. The inner heat exchanger housing 20 is formed with an interior vertical wall member 76 (FIG. 15) that defines a water flow channel or path 78 (FIGS. 13 and 15) which extends vertically along one side of the heat exchanger housing 20. The lower end of the water flow path 78 communicates with the interior of the water inlet nozzle 38. The upper end of the water flow path 78 communicates through a port 80 (FIG. 15) into the upper interior of the housing 20. This permits the incoming heat exchange water to be disbursed around the upper ends of the thousands of micro-conduits or fibers 50 of the heat exchanger fiber bundle 26. As previously explained, this water flows down around the outside of the fibers 50, through another port 82, and then out through water outlet nozzle 40. The opening of the nozzle 40 is shown at 84 in FIG. 15.

Figure 17:
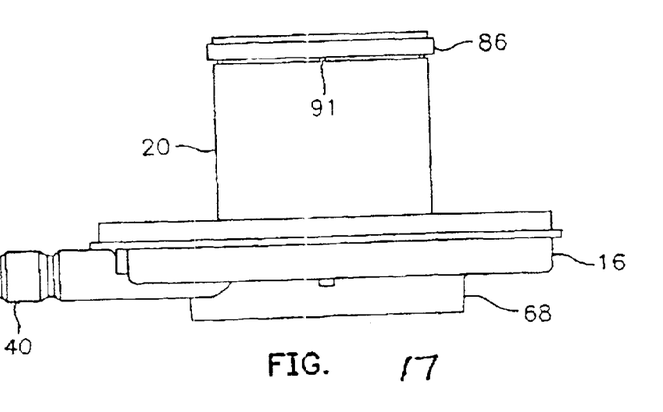
FIG. 17 is a side elevation view of the lower venous gas header and inner heat exchanger housing of the blood oxygenator.

The upper end of the cylindrical heat exchanger housing 20 is molded with a fitting ring 86 (FIGS. 15 and 17) having an upwardly opening circular recess 88 (FIG. 18) for receiving, and interfitting with, a downwardly extending circular flange of the outer heat exchanger housing 22. The fitting ring 86 is connected to the main part of the housing 20 by small plastic extensions 91 (FIG. 17).

Except for the fiber bundles 26 and 28, and the potting compound comprising the seals 92, 94, 106 and 108, the remainder of the structures illustrated and described herein are preferably injection molded of clear polycarbonate plastic. Suitable plastics are commercially available from Bayer under the designation MAKROLON and from General Electric under the designation LEXAN HP2R-1112. The separately molded plastic components may be assembled and permanently affixed to each other with a suitable non-toxic ultraviolet (UV) curable adhesive.

Figure 18:
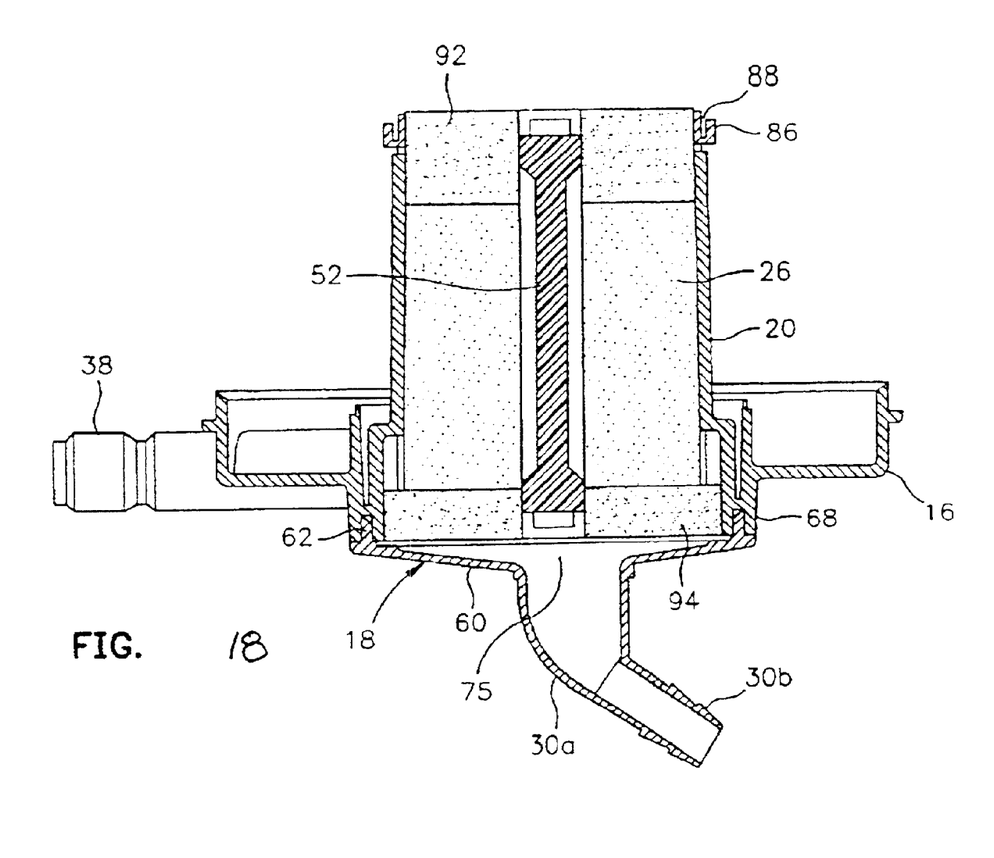
FIG. 18 is an enlarged vertical sectional view of the lower venous gas header and the inner heat exchanger housing with the blood inlet manifold connected. Also illustrated in this view is the micro-conduit fiber bundle of the heat exchanger.
Figure 19:
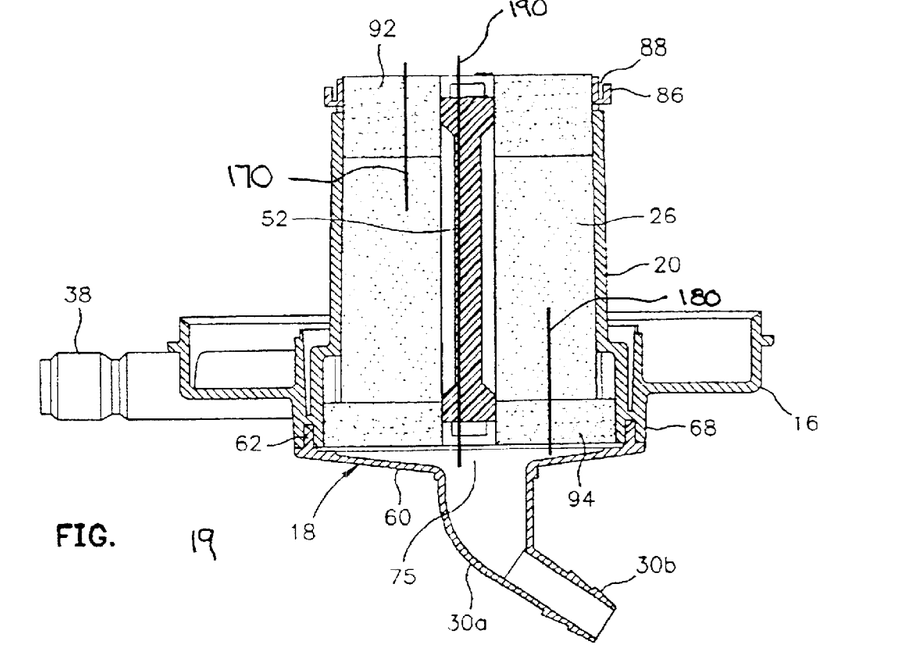
FIG. 19 is a view similar to FIG. 18 but showing several embodiments of the invention.

Some preferred embodiments of the invention are illustrated schematically in FIG. 19, which generally corresponds to FIG. 18 with like numbered components corresponding to components as described above. Several embodiments are shown. Potting 92 and/or potting 94 may be electrically conductive as described above. Or, a conductive wire or fiber may be introduced into the potting material as shown at 170 and 180. It would generally be preferred to locate the conductive wire or fiber as close to the outer periphery of the device as possible to facilitate visual inspection.

Alternatively, a conductive material 190 may be incorporated into the manufacture of the central spindle 52 to connect the blood side and the heat exchange fluid side.

As shown in FIG. 19, the conductive materials 170, 180 and 190 extend beyond the upper and lower ends of the potting material, but this is for illustrative purposes only. In any of these embodiments, it would be preferred to have the conductive material end flush with the cut surface of the potting, however, if the conductive material were stainless steel (as would be preferred for biocompatibility reasons), it might be difficult to cut the conductive material flush with the currently preferred manufacturing tools. A carbon fiber would be an alternative, but not necessarily a preferred one due to toxicity concerns. A conductor of any type inside the spindle 52 might be sealed by the potting process and not protrude a sufficient distance.

Figure 20:
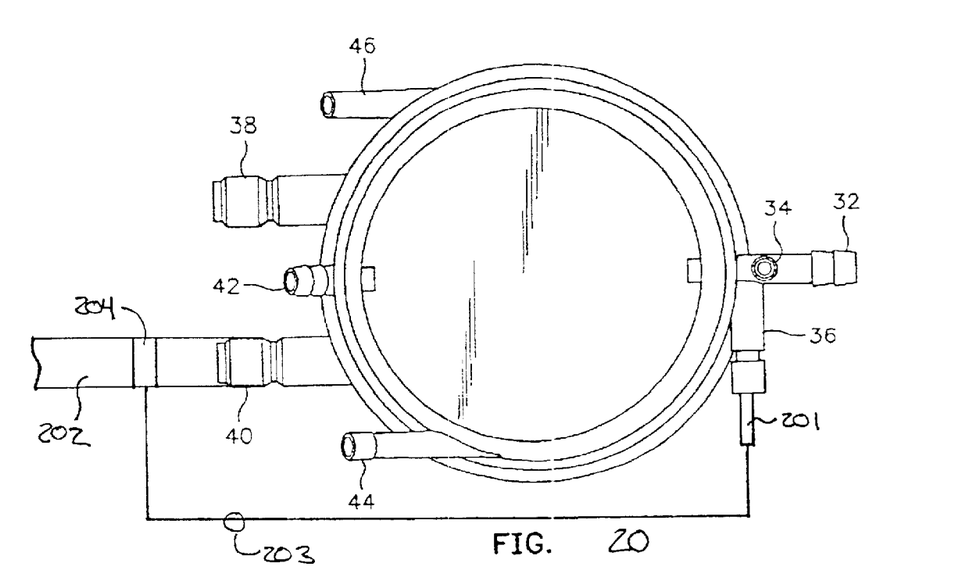
FIG. 20 is a view similar to FIG. 4 and additionally showing a preferred embodiment of the invention suitable for field installation with existing oxygenators.

To implement the invention on a previously manufactured MAXIMA FORTÉ oxygenator, a preferred embodiment is shown in FIG. 20 which generally corresponds to FIG. 4 with like numbered components corresponding to components as described above. FIG. 20 additionally shows temperature sensor 201 in the blood line and water line 202 connected to the oxygenator at water outlet 40. As noted earlier, any convenient type of electrical bridge 203 can be connected between temperature sensor 201 and an appropriate fitting (brass, stainless steel, etc.) 204 in water line 202. Of course, the water line (not shown) for water inlet 38 could have been chosen for the fitting 204 and connection to electrical bridge 203.

Other embodiments of the invention include a conductive wire, fiber, or ribbon woven into the mat of polymeric tubing comprising the heat exchanger bundle; or a bundle comprising conductive polymeric fibers themselves.

We claim:

1. A heat exchanger for physiologic fluids, comprising a polymeric heat transfer material separating the heat exchanger into two sides, a shell side and a tube side and an electrical bridge attached to said shell and to said tube said.

2. A method of reducing potential leakage in a heat exchanger having a polymeric heat transfer material between a tube side and a shell side, comprising the step of creating at least one electrical bridge between the tube side and the shell side.

3. A method of reducing potential leakage in a heat exchanger having a polymeric heat transfer material between a tube side and a shell side, comprising the step of providing an electrical bridge, between the tube side and the shell side, which reduces the charge differential between the tube side and the shell side to a level below that at which charge-induced failure of the polymeric material occurs.

4. The heat exchanger of any of claims 1, 2 or 3, in which the electrical bridge further comprises a single point connection to earth ground.

5. The heat exchanger of any of claims 1, 2 or 3, in which the electrical bridge further comprises a multipoint connection to earth ground.

6. The heat exchanger of any of claims 1, 2 or 3, in which the electrical bridge further comprises at least one fusible linkage.

7. The heat exchanger of any of claims 1, 2 or 3, in which the electrical bridge produces a common potential between the shell side and the tube side which is less than a breakdown voltage of the polymeric material.

8. The heat exchanger of any of claims 1, 2 or 3, in which the electrical bridge produces a common potential between the shell side and the tube side which avoids creating electrical interference in nearby medical instruments.

9. The heat exchanger of any of claims 1, 2 or 3, in which the electrical bridge produces a common potential between the shell side and the tube side which avoids adverse electrical hazards to the patient.

10. The heat exchanger of any of claims 1, 2 or 3, in which the electrical bridge produces a earth ground.

11. The heat exchanger of any of claims 1, 2 or 3, further comprising an electrical bridge between the tube side and earth ground.

12. The heat exchanger of any of claims 1, 2 or 3, further comprising an electrical bridge between the shell side and earth ground.

13. The heat exchanger of any of claims 1, 2 or 3, further comprising a plurality of electrical bridges between the tube side and the shell side and earth ground.

14. The heat exchanger of any of claims 1, 2 or 3, in which the electrical bridge comprises a wire.

15. The heat exchanger of any of claims 1, 2 or 3, in which the electrical bridge comprises a conductive ribbon.

16. The heat exchanger of any of claims 1, 2 or 3, in which the electrical bridge comprises a conductive film.

17. The heat exchanger of any of claims 1, 2 or 3, in which the electrical bridge has strain relief against thermal expansion and contraction.

18. The heat exchanger of any of claims 1, 2 or 3, in which the electrical bridge has strain relief against mechanical retention.

19. The heat exchanger of any of claims 1, 2 or 3, in which the electrical bridge comprises at least one coil.

20. The heat exchanger of any of claims 1, 2 or 3, in which the electrical bridge comprises at least one sinusoidal pattern.

21. The heat exchanger of any of claims 1, 2 or 3, in which the electrical bridge comprises at least one Z-shaped fold.

22. The heat exchanger of any of claims 1, 2 or 3, in which the electrical bridge comprises at least one swagged shapes.

23. The heat exchanger of any of claims 1, 2 or 3, in which the electrical bridge is insert molded into a plastic casing of the heat exchanger.

24. The heat exchanger of any of claims 1, 2 or 3, in which the electrical bridge comprises a part manufactured from an electrically conductive material.

25. The heat exchanger of any of claims 1, 2 or 3, in which the electrical bridge comprises a conductive ink.

26. The heat exchanger of any of claims 1, 2 or 3, in which the electrical bridge comprises a conductive paint.

27. The heat exchanger of any of claims 1, 2 or 3, in which the electrical bridge comprises a metallized fiber.

28. The heat exchanger of any of claims 1, 2 or 3, in which the electrical bridge comprises a metallized screen.

29. The heat exchanger of any of claims 1, 2 or 3, in which the electrical bridge comprises a multilayer construction.

30. The heat exchanger of any of claims 1, 2 or 3, in which the electrical bridge comprises an electrically conductive plastic.

31. The heat exchanger of any of claims 1, 2 or 3, in which the electrical bridge comprises an electrically conductive polymer.

32. The heat exchanger of any of claims 1, 2 or 3, in which the electrical bridge comprises an inherently conductive material.

33. The heat exchanger of any of claims 1, 2 or 3, in which the electrical bridge comprises an electrically conductive filler material.

34. The heat exchanger of any of claims 1, 2 or 3, in which the electrical bridge comprises an electrically permeable membrane.

35. The heat exchanger of any of claims 1, 2 or 3, in which the electrical bridge comprises an ionically permeable membrane.

36. The heat exchanger of any of claims 1, 2 or 3, in which the electrical bridge comprises a metal conductor imparted with a material having a lower dielectric constant than the polymeric fiber wall material.

37. The heat exchanger of any of claims 1, 2 or 3, in which the electrical bridge comprises a metal conductor coated with a material having a lower dielectric constant than the polymeric fiber wall material.

38. The heat exchanger of any of claims 1, 2 or 3, in which the electrical bridge is tailored to provide a dielectric constant.

39. The heat exchanger of any of claims 1, 2 or 3, in which the electrical bridge comprises a material having a lower dielectric constant than the polymeric fiber wall material.

40. The heat exchanger of any of claims 1, 2 or 3, in which the electrical bridge comprises a fusible material such that electrical current interrupts the link.

41. The heat exchanger of any of claims 1, 2 or 3, in which the electrical bridge comprises a material such that electrical current melts to interrupt the electrical bridge.

42. The heat exchanger of any of claims 1, 2 or 3, in which the electrical bridge comprises a metal conductor imparted with a material having a lower dielectric constant than the polymeric fiber wall material.

43. The heat exchanger of any of claims 1, 2 or 3, in which the electrical bridge further comprises an indication that a voltage potential is present.

44. The heat exchanger of any of claims 1, 2 or 3, in which the electrical bridge further comprises a visual indication that a voltage potential is present.

45. The heat exchanger of any of claims 1, 2 or 3, in which the electrical bridge further comprises an electromagnetic indication that a voltage potential is present.

46. The heat exchanger of any of claims 1, 2 or 3, in which the electrical bridge further comprises a change of color to indicate that a voltage potential is present.

47. The heat exchanger of any of claims 1, 2 or 3, in which the electrical bridge further comprises an auditory indication that a voltage potential is present.

48. The heat exchanger of any of claims 1, 2 or 3, in which the electrical bridge further comprises an analog signal to indicate that a voltage potential is present.

49. The heat exchanger of any of claims 1, 2 or 3, in which the electrical bridge further comprises a digital signal to indicate that a voltage potential is present.

50. The heat exchanger of any of claims 1, 2 or 3, in which the electrical bridge comprises at least one location physically remote from, but electrically common to, the tube side of the heat exchanger.

51. The heat exchanger of any of claims 1, 2 or 3, in which the electrical bridge comprises at least one location physically remote from, but electrically common to, the shell side of the heat exchanger.

52. The heat exchanger of any of claims 1, 2, or 3, in which the electrical bridge comprises at least one location physically remote from, but electrically common to both the tube side and the shell side of the heat exchanger.

53. The heat exchanger of any of claims 1, 2 or 3, in which the electrical bridge comprises a connection to the tube side fluid in the form of a metal probe.

54. The heat exchanger of any of claims 1, 2 or 3, in which the electrical bridge comprises a connection to the tube side fluid in the form of a metal temperature sensor.

55. The heat exchanger of any of claims 1, 2 or 3, in which the electrical bridge comprises a connection to the tube side fluid in the form of a metal probe located downstream of the heat exchanger.

56. The heat exchanger of any of claims 1, 2 or 3, in which the electrical bridge comprises a connection to the tube side fluid in the form of a metal temperature sensor located downstream of the heat exchanger.

57. The heat exchanger of any of claims 1, 2 or 3, in which the electrical bridge comprises a connection to the shell side fluid in the form of a metal probe.

58. The heat exchanger of any of claims 1, 2 or 3, in which the electrical bridge comprises a connection to the shell side fluid in the form of a metal temperature sensor.

59. The heat exchanger of any of claims 1, 2 or 3, in which the electrical bridge comprises a connection to the shell side fluid in the form of a metal probe located downstream of the heat exchanger.

60. The heat exchanger of any of claims 1, 2 or 3, in which the electrical bridge comprises a connection to the shell side fluid in the form of a metal temperature sensor located downstream of the heat exchanger.

61. The heat exchanger of any of claims 1, 2 or 3, in which the electrical bridge comprises a conductive thread.

62. The heat exchanger of any of claims 1, 2 or 3, in which the electrical bridge comprises a conductive stainless steel thread.

63. The heat exchanger of any of claims 1, 2 or 3, in which the electrical bridge comprises a conductive carbon thread.

64. The heat exchanger of any of claims 1, 2 or 3, in which the electrical bridge comprises a conductive thread located inside the heat exchanger.

65. The heat exchanger of any of claims 1, 2 or 3, in which the electrical bridge comprises a conductive stainless steel thread located inside the heat exchanger.

66. The heat exchanger of any of claims 1, 2 or 3, in which the electrical bridge comprises a conductive carbon thread located inside the heat exchanger.

67. The heat exchanger of any of claims 1, 2 or 3, in which the electrical bridge comprises an electrically conductive material placed next to the polymeric heat exchanger.

68. The heat exchanger of any of claims 1, 2 or 3, in which the electrical bridge comprises an electrically conductive material placed within a mat of polymeric fibers.

69. The heat exchanger of any of claims 1, 2 or 3, in which the electrical bridge comprises an electrically conductive material placed within a mat of polymeric fibers prior to assembly of the heat exchanger bundle.

70. The heat exchanger of any of claims 1, 2 or 3, in which the electrical bridge comprises an electrically conductive potting material.

71. The heat exchanger of any of claims 1, 2 or 3, in which the electrical bridge comprises a conductive material woven into a mat of polymeric tubing comprising a heat exchanger bundle.

72. The heat exchanger of any of claims 1, 2 or 3, in which the electrical bridge comprises a polymeric fiber bundle in which at least some of the polymeric fibers are conductive.

73. A heat exchanger for physiologic fluids, comprising a polymeric heat transfer material separating the heat exchange into two sides, a shell side and a tube side and an electrical bridge attached to said shell and to said tube side, the electrical bridge comprising a floating ground.

74. A method of reducing potential leakage in a heat exchanger having a polymeric heat transfer material between a tube side and a shell side, comprising the step of creating at least one electrical bridge between the tube side and the shell side, the electrical bridge comprising a floating ground.

75. A method of reducing potential leakage in a heat exchanger having a polymeric heat transfer material between a tube side and a shell side, comprising the step of providing an electrical bridge comprising a floating ground between the tube side and the shell side, which reduces the charge differential between the tube side and the shell side to a level below that at which charge-induced failure of the polymeric material occurs.

76. The heat exchanger of any of claims 73, 74, or 75, in which the electrical bridge comprises a wire.

77. The heat exchanger of any of claims 73, 74, or 75, in which the electrical bridge comprises a conductive ribbon.

78. The heat exchanger of any of claims 73, 74, or 75, in which the electrical bridge comprises a conductive film.

79. The heat exchanger of any of claims 73, 74, or 75, in which the electrical bridge comprises a part manufactured from an electrically conductive material.

80. The heat exchanger of any of claims 73, 74, or 75, in which the electrical bridge comprises a conductive ink.

81. The heat exchanger of any of claims 73, 74, or 75, in which the electrical bridge comprises a conductive paint.

82. The heat exchanger of any of claims 73, 74, or 75, in which the electrical bridge comprises a metallized fiber.

83. The heat exchanger of any of claims 73, 74, or 75, in which the electrical bridge comprises a metallized screen.

84. The heat exchanger of any of claims 73, 74, or 75, in which the electrical bridge comprises an electrically conductive plastic.

85. The heat exchanger of any of claims 73, 74, or 75, in which the electrical bridge comprises an electrically permeable membrane.

86. The heat exchanger of any of claims 73, 74, or 75, in which the electrical bridge comprises an ionically permeable membrane.

87. The heat exchanger of any of claims 73, 74, or 75, in which the electrical bridge comprises a conductive thread.

88. A heat exchanger for physiologic fluids, comprising a polymeric heat transfer material separating the heat exchange into two sides, and means for making a floating ground electrical bridge between the two sides.

* * * * *

UNITED STATES PATENT AND TRADEMARK OFFICE
CERTIFICATE OF CORRECTION

PATENT NO. : 6,497,841 B1  Page 1 of 1
APPLICATION NO. : 08/898559
DATED : December 24, 2002
INVENTOR(S) : Neil D. Plotkin et al.

It is certified that error appears in the above-identified patent and that said Letters Patent is hereby corrected as shown below:

Column 12, line 32, that portion of the claim reading "said shell and to said tube said" should read --said shell side and to said tube side--.

Column 16, line 2, that portion of the claim reading "said shell and" should read --said shell side and--.

Signed and Sealed this

Twentieth Day of February, 2007

JON W. DUDAS
*Director of the United States Patent and Trademark Office*